United States Patent [19]
Dakashinamurti et al.

[11] Patent Number: 6,051,587
[45] Date of Patent: Apr. 18, 2000

[54] TREATMENT OF IATROGENIC AND AGE-RELATED HYPERTENSION AND PHARMACEUTICAL COMPOSITIONS USEFUL THEREIN

[75] Inventors: Krishnamurti Dakashinamurti; Rajat Sethi; Naranjan S. Dhalla, all of Manitoba, Canada

[73] Assignees: Medicure, Inc.; The University of Manitoba, both of Winnipeg, Canada

[21] Appl. No.: 09/061,173

[22] Filed: Apr. 16, 1998

[51] Int. Cl.[7] .......................... A61K 31/44; A61K 31/195
[52] U.S. Cl. ............................................. 514/345; 514/567
[58] Field of Search ...................................... 514/345, 567

[56] References Cited

U.S. PATENT DOCUMENTS

| | | |
|---|---|---|
| 4,374,841 | 2/1983 | Deschamps et al. . |
| 4,564,614 | 1/1986 | Crawford et al. ...................... 514/222 |

OTHER PUBLICATIONS

The Effects of Vitamin B6 on the Systolic Blood Pressure of Rats in Various Animal Models of Hypertension, Lal et al., Journal of Hypertension 1996, vol. 14, No. 3, 355–362.

Hypotensive Action of 5–HT Receptor Agonists in the Vitamin B6–Deficient Hypertensive Rat, Lal et al., European Journal of Pharmacology, 234(1993) 183–189.

Sympathetic Stimulation and Hypertension in the Pyridoxine–Deficient Adult Rat, Paulose et al., Journal of Hypertension, 1988, vol. 11, No. 4, 387–391.

Calcium Channels in Vitamin B6 Deficiency–Induced Hypertension, Lal et al., Journal of Hypertension 1993, vol. 11, No. 12, 1357–1362.

*Primary Examiner*—Zohreh Fay
*Attorney, Agent, or Firm*—Stevens, Davis, Miller & Mosher, L.L.P.

[57] ABSTRACT

Hypertension in mammalian patients, especially elderly human patients, derived from ingestion of NSAIDs or through the normal aging process is treated by administration to the patient of a vitamin $B_6$ (or derivative) supplement. Where the patient requires the continued administration of an NSAID for pharmacological purposes, the NSAID is administered in conjunction with a vitamin $B_6$ supplement. The invention further provides combination pharmaceutical combinations of an NSAID and a vitamin $B_6$ supplement, e.g. orally administrable tablets or capsules, for use in treating such conditions.

10 Claims, No Drawings

TREATMENT OF IATROGENIC AND AGE-RELATED HYPERTENSION AND PHARMACEUTICAL COMPOSITIONS USEFUL THEREIN

FIELD OF THE INVENTION

This invention relates to pharmaceutical compositions and combinations, and uses thereof in medical treatment. More specifically, it relates to treatment of hypertension and to pharmaceutical compositions and combinations useful therein, especially treatment of hypertension in human patients on NSAID treatment.

BACKGROUND OF THE INVENTION

The occurrence of hypertension (elevated blood pressure) in the elderly is high. This is also the age group with a high incidence of arthritis. Osteo-arthritis is common after the age of 40. The presence of an inflammatory component to osteo-arthritis is now recognized. About 30% of patients with arthritis also have hypertension. Thus there is a considerable potential for the concurrent prescription of non-steroidal anti-inflammatory drugs (NSAIDs) and anti-hypertensives in the elderly population group. It is estimated that, in the United States, more than 20 million people are on concurrent anti-hypertensive and NSAID therapy. It is known that most anti-hypertensive agents are less effective in the presence of NSAIDs.

In the past several years, there have been various reports of adverse effects of NSAIDs in patients receiving any form of anti-hypertensive medication such as β-blockers, angiotensin converting enzyme inhibitors and diuretics. The hypotensive (blood pressure lowering) effect of β-blockers is attenuated by the combined administration of NSAIDs such as indomethacin, sulindac and piroxicam. Significant attenuation of the hypotensive effect of the angiotensin-converting enzyme inhibitor captopril by indomethacin, acetylsalicylate and sulindac has been reported. The antagonism by NSAIDs of the hypotensive effects of diuretics such as furosemide and hydrochlorothiazide has also been reported. Naproxen and piroxicam have been reported to raise blood pressure of patients significantly during the concomitant use of drugs such as β-blockers and diuretics. Most NSAIDs appear to reduce the anti-hypertensive effect of a variety of anti-hypertensive drugs, with the exception of the calcium channel blockers, which in any event have recently been reported to have other adverse side effects. Patients with renal impairment are at a risk of developing renal side effects when NSAIDs are used. In the elderly population suffering from various arthritic disorders, the potential adverse interaction between anti-inflammatory and anti-hypertensive drugs poses a significant problem. Treatments that maintain the anti-hypertensive action would be very beneficial to this age group.

BRIEF REFERENCE OF THE PRIOR ART

Paulose, C. S., Dakshinamurti, K., Packer, S. C., and Stephens, N. L., "Sympathetic Stimulation and Hypertension in the Pyridoxine-deficient Rat", Hypertension, Vol. 11, pages 387–391, 1988, reports work that shows that a moderate deficiency of vitamin $B_6$ in rats causes hypertension which is reversed within 24 hours by the administration of vitamin $B_6$ in the form of pyridoxine.

U.S. Pat. No. 4,374,841 reports that pyridine derivatives such as 4,5-dihydroxymethyl-3-[2-hydroxy-3-(2-methylphenoxyethylamino)-propoxy]-2-methylpyridine and 4,5-dihydroxyethyl-3-[2-hydroxy-3-(2-methoxyphenoxyethylamino)-propoxy]-2-methyl-pyridine reduce the epinephrine-increased blood pressure in dogs.

Some nutritional studies, namely Vanderjagt, D. J. and Garry, P. J., "Vitamin $B_6$ Status in a Health Elderly Population", Ann. N.Y. Acad. Sci., Vol. 585, page 562–564, 1990, and Kok, F. J. et al., "Low Vitamin $B_6$ Status in Patients with Acute Myocardial Infarction", Am. J. Cardiol., Vol. 63. pages 513–516, 1989, indicate that the elderly may be at increased risk for developing a deficiency of vitamin $B_6$.

It is an object of the present invention to provide novel pharmaceutical combinations which are useful in treating hypertension in patients.

It is a further and more specific object to provide combinations of NSAIDs with other pharmaceutical, which can be used for treating hypertension without serious loss of the anti-inflammatory activity of the NSAID.

It is a further object to provide novel treatments of hypertension in patients suffering therefrom and under NSAID treatment, especially in adult human patients.

SUMMARY OF THE INVENTION

The present invention is based upon the discovery that vitamin $B_6$ and derivatives thereof attenuate the hypertension induced by anti-inflammatory drugs such as the NSAIDs. Blood pressure in hypertensive mammals is significantly and rapidly reduced by administration to the patient of vitamin $B_6$ or derivative supplement. Meta analysis of various studies indicates that the ingestion of NSAIDs attenuates the anti-hypertensive effect of a variety of anti-hypertensive drugs such as β-blockers, angiotensin-converting enzyme inhibitors and diuretics, which reduces or even negates the usefulness of such drugs as anti-hypertensives when NSAIDs are also used.

Thus according to one aspect of the present invention, there is provided a method of alleviating hypertension in a mammalian patient who has hypertension under treatment by NSAIDs, which comprises administering to the patient an effective amount of a vitamin $B_6$ supplement or vitamin $B_6$ derivative supplement.

According to another aspect, the present invention provides a process of treating a mammalian patient in need of the beneficial effects of a non-steroidal anti-inflammatory drug (NSAID) without causing excessive hypertension in the patient, which comprises administering to the patient an effective amount of an NSAID in conjunction with a vitamin $B_6$ supplement or vitamin $B_6$ derivative supplement.

According to a further aspect, the invention provides pharmaceutical compositions for treating NSAID-induced hypertension in aged mammalian patients, comprising an effective amount of a vitamin $B_6$ supplement or vitamin $B_6$ derivative supplement.

DESCRIPTION OF THE PREFERRED EMBODIMENTS

Since elderly human patients commonly suffer from osteo and rheumatoid arthritis or similar conditions for which NSAIDs are the recommended treatment, and since elderly patients commonly suffer from hypertension, the present invention is particularly suitable for use with elderly human patients, and this is its preferred application. Thus it is of particular significance under conditions (i) where the patient is ingesting anti-inflammatory drugs, including over-the-counter anti-inflammatory drugs, e.g. for treatment of osteo or rheumatoid arthritis, and (ii) in age-related hypertension in the elderly. However, the invention is not so limited and provides beneficial effects for substantially all mammalian patients suffering from hypertension.

The range of NSAIDs which can be beneficially included in the compositions and treatments according to the present invention is very wide, and extends to substantially all of the known NSAIDs currently available on the market. Specific NSAIDs which may be used in the present invention include diclofenac, indomethacin, the various anti-inflammatory acetylsalicylates (e.g. aspirin), sulindac, alclofenac, amfenac, piroxicam, naproxen, fenoprofen, ibuprofen, ketoprofen, flurbiprofen, alminoprofen, ketorolac, GOBAB (3-amino-4-hydroxybutyric acid), amixetrine, diflunisal, mefenamic acid, phenylbutazone, tiaprofenic acid and tolmetin. Specifically preferred are diclofenac, indomethacin and the acetylsalicylates.

The vitamin $B_6$ derivatives contemplated for use in the present invention are those which are chemical modifications of vitamin $B_6$, sometimes formed in the body as metabolites thereof, and having the same ring nucleus, for example pyridoxal-5-phosphate, pyridoxal, pyridoxamine, 4-pyridoxic acid, etc.

The vitamin $B_6$ supplement used in the present invention is preferably pyridoxine in any of its pharmaceutically acceptable forms, such as pyridoxine hydrochloride addition salt. The amount of vitamin $B_6$ compound or supplement used in the present invention is preferably from about 10 mg to about 500 mg, most preferably from about 50 to about 100 mg, per 70 kg of body weight of the patient, of vitamin $B_6$ pyridoxine hydrochloride, or related compound acting as a vitamin $B_6$ (or derivative) supplement, for administration on a daily or twice daily basis, to an adult human patient.

The amount of NSAID administered to the patient, in the process of the invention, does not normally change from the prescribed dosage being used to treat the inflammatory condition in the absence of the vitamin $B_6$ (or derivative) supplement. Thus, a patient taking a daily dosage of, say, 500 mg of naproxen to treat or alleviate an underlying inflammatory condition continues to take the same prescribed 500 mg thereof supplemented by vitamin $B_6$ or derivative in the process of the invention. Suitable prescribed doses vary widely according to the chose of NSAID, the underlying conditions it is intended to alleviate, and factors concerning the individual patient. Generally appropriate dosage ranges may be found by consulting standard reference pharmacopeias, and thus are well within the skill of the art. As examples, indomethacin is commonly prescribed for rheumatoid arthritis at an oral dosage rate of 75–200 mg per day, in three separate doses per day. Diclofenac is commonly prescribed for rheumatoid arthritis and osteoarthritis, at a daily oral dosage rate of 75–150 mg, in three separate doses per day. Acetylsalicylates are generally administered in higher dosages, such as 650 mg, four to six times per day as necessary to alleviate the symptoms. The same NSAID dosage rates as prescribed, are continued in the process and formulations of the invention.

A specific preferred embodiment of the present invention is a dosage form pharmaceutical composition for administration to patients requiring NSAID therapy, comprising in combination an effective amount of an NSAID and an amount of vitamin $B_6$ (or derivative) supplement effective to alleviate the hypertensive effects of the NSAID. Such a formulation suitably takes the form of an orally administrable tablet or capsule, with appropriate inert, table forming ingredients. The amount of NSAID in such a tablet or capsule may be in the range of 25–1000 mg, depending on choice of NSAID, condition to be treated, frequency of administration, etc. The amount of vitamin $B_6$ (or derivative) supplement in such a tablet or capsule may be in the range 10–500 mg. Such a combined drug formulation provides effective therapy upon administration.

Whilst it is most convenient and preferred to prepare and use compositions which comprise a combination of the NSAID and the vitamin $B_6$ or derivaative, e.g., in a tablet or capsule form, along with suitable pharmaceutical carriers, diluents, excipients and the like, for oral administration, other methods of administration are within the scope of the present invention. For example, the active ingredients, namely the NSAID and vitamin $B_6$ or derivative, may be administered separately and sequentially to the patient, and the combined or sequential administration may be via the oral route, or alternatively parenterally, intramuscularly, rectally, transcutaneously or nasally. Formulations of the compositions of the present invention for such forms of administration are standard and within the skill of the pharmaceutical compounders art.

Vitamin $B_6$ is a known but not commonly prescribed anti-hypertensive agent, although not previously known to be effective in the present of NSAIDs. A substantial advantage of its use is that it is known to be non-toxic and to lack side effects in the proposed human dosage of up to 600 mg/person/day, having previously been so used, for example, in long term treatment of chronic anemia.

SPECIFIC EXAMPLES

The following specific examples further describe and illustrate the present invention and its use, but are not to be construed as limiting on the scope of the invention. They describe the invention is relation to its use on laboratory animals, in accordance with approved practices. Laboratory rats, some having a moderate hypertension condition and some being normal, normotensive rates were used, taking measurements of their systolic blood pressure in acute and long term experiments using compositions according to the invention. The hypertensive rats were on a vitamin $B_6$ deficient diet for 8–10 weeks prior to the experiments. They has a body weight of 200–225 g. The control normotensive rats weighed about 300 g.

Example 1

Control

The time and dosage response of hypertensive rats to treatment with diclofenac was investigated.

Vitamin $B_6$ deficiency-induces hypertensive rats (prepared according to the procedures of Paulose et al., cited above) were used in acute experiments. They were injected with varying doses of diclofenac and the changes in systolic blood pressure (SBP) were monitored by tail cuff plethysmography. In vitamin $B_6$-deficient hypertensive rats (SBP, 150 mm Hg), intraperitoneal injection of diclofenac sodium (dose, 1 mg/kg body weight) raised the SBP by 9 mm Hg in one hour after injection. A higher dose (3 mg/kg) elevated SBP by 28 mm Hg, which also occurred one hour after injection. A larger dose (10 mg/kg) caused an increase of SBP of similar magnitude but the effect lasted for 2 hours.

Example 2

Control

The effects of treatment with indomethacin on the SBP of hypertensive rats was investigated.

The effect of varying doses (1 or 3 mg/kg body weight) of indomethacin on the SBP of hypertensive rats was examined by monitoring SBP tail cuff plethysmography following intraperitoneal injection of the drug or vehicle to the rats. Indomethacin (3 mg/kg) raised the blood pressure of hypertensive rats by 6 mm Hg within thirty minutes. The peak response (35 mm Hg) was reach by one hour. Although the effect declined by two hours, it was still elevated (15 mm Hg) and vehicle injected levels were reached only after three hours. A smaller dose (1 mg/kg) did not have any effect on the SBP of the hypertensive rat.

In the following Example 3, 4 and 5, the effects of oral administration of various NSAIDs up to seven days on the SBP of rats on a normal diet were examined. Older (chronological age) normal rats (400–600 g body weight) on a commercial rat diet (chow) were used. These rats has a SBP of 145–150 mm Hg.

Example 3

The effect of oral administration of a vitamin $B_6$ supplement (2.5 or 5 times the daily requirement) on SBP of older rats was examined. The rats were divided into four groups. Group 1 was continued on the same commercial rat chow ration. Group 2 was fed the same diet containing diclofenac (100 mg per kg diet). Group 3 was fed the commercial rat chow diet containing a vitamin $B_6$ supplement (2.5 or 5 times the daily requirement for vitamin $B_6$, i.e. 25 mg/kg and 50 mg/kg respectively). Group 4 was fed diclofenac as in Group 2 but also has the vitamin $B_6$ supplement in the same amounts. The animals consume about 15 grams of chow per day. The SBPs were determined on days 0 (6 hours after start of feeding), 1 and 7, at the same time (late afternoon) for each measurement. The results are given in Tables 1(a) for 2.5 times vitamin $B_6$ supplement and in Table 1(b) for 5 times vitamin $B_6$ supplement. In the Tables, each value is the mean±S.E.M. of 5 rats. Body weight is indicated by B.Wt., systolic blood pressure by SPB and heart rate by HR.

TABLE 1(a)

| | 0 Day on Diet | | | 1 Day on Diet | | | 7 Days of Diet | | |
|---|---|---|---|---|---|---|---|---|---|
| Group | B. Wt. (g) | SBP (mm Hg) | HR (beat/min) | B. Wt. (g) | SBP (mm Hg) | HR (beat/min) | B. Wt. (g) | SBP (mm Hg) | HR (beat/min) |
| 1 | 413 ± 6 | 145 ± 1 | 345 ± 5 | — | 148 ± 2 | 350 | 418 ± 18 | 146 ± 1 | 345 ± 5 |
| 2 | 414 ± 15 | 145 ± 2 | 335 ± 10 | — | 148 ± 1 | 345 ± 5 | 418 ± 20 | 147 ± 1 | 330 ± 5 |
| 3 | 431 ± 7 | 146 ± 1 | 350 ± 9 | — | 135* ± 1 | 345 ± 5 | 446 ± 9 | 136* ± 1 | 325 ± 11 |
| 4 | 415 ± 6 | 145 ± 2 | 345 ± 5 | — | 123* ± 2 | 335 ± 13 | 416 ± 11 | 120* ± 2 | 325 ± 8 |

*P < 0.05 with respect to normal chow or normal chow plus Diclofenac (100 mg/kg diet)

TABLE 1(b)

| | 0 Day on Diet | | | 1 Day on Diet | | |
|---|---|---|---|---|---|---|
| Group | B. Wt. (g) | SBP (mm Hg) | HR (beat/min) | B. Wt. (g) | SBP (mm Hg) | HR (beat/min) |
| 1 | 565 ± 15 | 148 ± 1 | 345 ± 10 | — | 147 ± 1 | 350 ± 10 |
| 2 | 560 ± 13 | 148 ± 1 | 350 ± 12 | — | 149 ± 1 | 350 ± 10 |
| 3 | 563 ± 16 | 148 ± 1 | 350 ± 8 | — | 124* ± 1 | 350 ± 10 |
| 4 | 561 ± 12 | 149 ± 1 | 330 ± 8 | — | 108* ± 1 | 335 ± 8 |

*P < 0.05 with respect to normal chow or normal chow plus Diclofenac (100 mg/kg diet)

These results indicate that, even on day 1, vitamin $B_6$ supplementation alone gives a significant decrease in SBP (Group 3 results in comparison with Group 1 results). Diclofenac alone had little effect (Group 2 results), but the combination of vitamin $B_6$ supplement and diclofenac (Group 4) was most marked. Vitamin $B_6$ supplement decreased the SBP of older rats. The effect was quite significant even when the rats were receiving diclofenac. The higher dose of vitamin $B_6$ resulted in a larger effect. The effect of vitamin $B_6$ supplementation was seen as early as one day after the treatment and was still seen one week after initiation of the supplementation regimen.

Example 4

The experiments reported in Example 3 were essentially repeated using a different et of essentially the same animals, but substituting indomethacin at the same amounts, for diclofenac. Each experiment used 1.5 times vitamin $B_6$ supplement. The results are given in Table 2, corresponding to the previous Tables.

TABLE 2

| Group | 0 Day on Diet | | | 1 Day on Diet | | | 7 Days of Diet | | |
|---|---|---|---|---|---|---|---|---|---|
| | B. Wt. (g) | SBP (mm Hg) | HR (beat/min) | B. Wt. (g) | SBP (mm Hg) | HR (beat/min) | B. Wt. (g) | SBP (mm Hg) | HR (beat/min) |
| 1 | 437 ± 8 | 149 ± 2 | 320 ± 12 | — | 150 ± 2 | 320 ± 15 | 467 ± 8 | 149 ± 1 | 325 ± 11 |
| 2 | 480 ± 24 | 150 ± 1 | 320 ± 12 | — | 150 ± 1 | 340 ± 19 | 411* ± 10 | 150 ± 2 | 331 ± 12 |
| 3 | 480 ± 17 | 148 ± 2 | 325 ± 11 | — | 134* ± 1 | 335 ± 6 | 521 ± 16 | 132* ± 5 | 355 ± 15 |
| 4 | 452 ± 7 | 148 ± 1 | 340 ± 10 | — | 124* ± 2 | 350 ± 18 | 408 ± 2 | 116* ± 1 | 344 ± 6 |

*$P < 0.05$ with respect to normal chow or normal chow plus Indomethacin (100 mg/kg diet)

These results are comparable to those reported in Table 1(a).

Vitamin $B_6$ supplementation decreased the SBP of rats. This was quite significant in rats getting indomethacin, in addition.

Example 5

In these experiments, the effects of the vitamin $B_6$ supplement 2.5 times the daily requirement) on the SBP of the older rats on commercial rat ration but receiving acetyl salicylate (20 or 100 mg per kg. diet) in the diet were investigated. The experiments were conducted as described in Example 1. Different sets of essentially the same animals were used. Table 3(a) reports the results with animals of four groups.

Group 1 was fed normal chow.

Group 2 was fed normal chow.

Group 3 was fed chow with 2.5×vitamin $B_6$.

Group 4 was fed chow with 2.5×vitamin $B_6$ plus acetylsalicylate (20 mg/kg diet).

Each Value is the Mean±S.E.M. of 5 rats.

As in the previous experiments, vitamin $B_6$ supplementation decreased the SBP of these rates. The effects were most significant in rats receiving the anti-inflammatory drug.

Example 6

The effect of diclofenac administration with and without co-administration of vitamin $B_6$ was studied in young hypertensive rats as described in Example 3, but using a daily dosage of diclofenac of 10 mg/kg and continuing the treatment for 60 days. As before, four groups of rats were used, each group comprising 6 animals. Group 1 received a normal commercial chow ration daily. Group 2 received the same chow ration daily, supplemented with the diclofenac. Group 3 received the same chow ration daily, supplemented with 25 mg/kg vitamin $B_6$. Group 4 received the same chow ration daily, supplemented with both diclofenac and vitamin $B_6$ at the aforesaid amounts. The results are given below in Table 4.

TABLE 3(a)

| Group | 0 Day on Diet | | | 1 Day on Diet | | | 7 Days of Diet | | |
|---|---|---|---|---|---|---|---|---|---|
| | B. Wt. (g) | SBP (mm Hg) | HR (beat/min) | B. Wt. (g) | SBP (mm Hg) | HR (beat/min) | B. Wt. (g) | SBP (mm Hg) | HR (beat/min) |
| 1 | 443 ± 13 | 150 ± 1 | 330 ± 9 | — | 150 ± 2 | 330 ± 12 | 450 ± 10 | 150 ± 2 | 325 ± 10 |
| 2 | 450 ± 11 | 150 ± 2 | 325 ± 11 | — | 150 ± 3 | 300 ± 12 | 416* ± 14 | 149 ± 1 | 315 ± 6 |
| 3 | 443 ± 21 | 148 ± 1 | 330 ± 9 | — | 137* ± 1 | 335 ± 10 | 456 ± 16 | 132* ± 1 | 300 ± 8 |
| 4 | 453 ± 13 | 149 ± 2 | 345 ± 5 | — | 124* ± 1 | 355 ± 15 | 367 ± 8 | 116* ± 1 | 340 ± 10 |

*$P < 0.05$ with respect to normal chow or normal chow plus acetylsalicylate

Table 3(b) reports similarly the results of experiments in which the Group 2 and Group 4 animals received 100 mg/kg acetylsalicylate instead of 20 mg/kg—otherwise the experiments were the same.

TABLE 3(b)

| Group | 0 Day on Diet | | | 1 Day on Diet | | | 7 Days of Diet | | |
|---|---|---|---|---|---|---|---|---|---|
| | B. Wt. (g) | SBP (mm Hg) | HR (beat/min) | B. Wt. (g) | SBP (mm Hg) | HR (beat/min) | B. Wt. (g) | SBP (mm Hg) | HR (beat/min) |
| 1 | 560 ± 10 | 149 ± 1 | 345 ± 10 | — | 149 ± 1 | 340 ± 10 | — | 149 ± 1 | 350 ± 10 |
| 2 | 558 ± 15 | 148 ± 2 | 350 ± 10 | — | 148 ± 1 | 350 ± 15 | — | 148 ± 1 | 350 ± 10 |
| 3 | 565 ± 10 | 148 ± 1 | 345 ± 10 | — | 136* ± 1 | 345 ± 10 | — | 133* ± 1 | 350 ± 11 |
| 4 | 555 ± 12 | 148 ± 1 | 350 ± 10 | — | 125* ± 1 | 340 ± 10 | — | 123* ± 1 | 350 ± 12 |

*$P < 0.05$ with respect to normal chow or normal chow plus acetylsalicylate.

TABLE 4

| Group | Day 0 | | Day 60 | |
| --- | --- | --- | --- | --- |
| | Body wt (g) | SBP | Body wt | SBP |
| 1 | 255 ± 12 | 121 ± 2 | 502 ± 10 | 151 ± 3 |
| 2 | 272 ± 14 | 125 ± 1 | 512 ± 12 | 169 ± 2 |
| 3 | 267 ± 14 | 131 ± 2 | 497 ± 16 | 123 ± 2 |
| 4 | 258 ± 13 | 127 ± 1 | 676 ± 13 | 138 ± 1 | n = 6,
P < 0.05 compared to Group 1 and Group 2,
P < 0.05 compared to Groups 1, 3 and 4.

The results reported in connection with these Examples lead to the conclusion that moderate vitamin $B_6$ deficiency causes a modest hypertension in mammals. The administration (i.p.) of non-steroidal anti-inflammatory drugs exacerbates the hypertension in acute experiments. Administration of vitamin $B_6$ or a derivative thereof attenuates the hypertensive potential of the NSAIDs. In longer term experiments the oral administration of a vitamin $B_6$ (or derivative) supplement to older mammals results in a significant decrease in the SBP of these mammals which were still receiving NSAIDs. The co-administration of vitamin $B_6$ (or derivatives) and NSAIDs results in a significant decrease in the SBP or older mammals.

We claim:

1. A method of alleviating hypertension in a hypertensive mammalian patient under treatment by at least one NSAID, which comprises administering to the patient an effective amount of a vitamin $B_6$ supplement selected from pyridoxine, pyridoxine hydrochloride, pyridoxyl, pyridoxyl-5-phosphate, pyridoxamine and 4-pyridoxic acid.

2. The method of claim 1 wherein the amount of vitamin $B_6$ supplement is from about 10 mg to about 500 mg per 70 kg of body weight of the patient.

3. A process of treating a mammalian patient suffering from hypertension and in need of the beneficial pharmacological effects of a non-steroidal anti-inflammatory drug (NSAID), which comprises administering to the patient an effective amount of an NSAID and an effective amount of a vitamin B6 supplement selected from pyridoxine, pyridoxine hydrochloride, pyridoxal, pyridoxal-5-phosphate, pyridoxamine and 4-pyridoxic acid.

4. The process of claim 3 wherein the NSAID is administered together with the vitamin $B_6$ supplement.

5. The process of claim 3 wherein the NSAID is administered separately from the vitamin $B_6$ supplement.

6. The process of claim 3 wherein the NSAID is selected from among diclofenac, indomethacin, acetylsalicylates, sulindac, alclofenac, amfenac, piroxicam, naproxen, fenoprofen, ibuprofen, ketoprofen, flurbiprofen, alminoprofen, ketorolac, GOBAB, amixetrine, diflunisal, mefenamic acid, phenylbutazone, tiaprofenic acid and tolmetin.

7. The process of claim 6, wherein the vitamin $B_6$ supplement is administered in an amount of from about 10 mg–500 mg per 70 kg body weight of the patient.

8. The method of claim 7 wherein the NSAID is diclofenac, indomethacin or an acetylsalicylate.

9. The process of claim 7, wherein the administration of the NSAID and the vitamin $B_6$ supplement is accomplished simultaneously, by oral administration of a capsule or tablet incorporating both the NSAID and the vitamin $B_6$ supplement.

10. The method of claim 1 wherein the NSAID is selected from the group consisting of diclofenac, indomethacin, acetylsalicylates, sulindac, alclofenac, amfenac, piroxicam, naproxen, fenoprofen, ibuprofen, ketoprofen, diflunisal, alminoprofen, ketorolac, GOBAB, amixetrine, flurbiprofen, mefenamic acid, phenylbutazone, tiaprofenic acid and tolmetin.

* * * * *